US005492839A

United States Patent [19]

Campbell et al.

[11] Patent Number: 5,492,839
[45] Date of Patent: Feb. 20, 1996

[54] IMMUNOGENIC RYANODINE DERIVATIVE AND RELATED USES

[75] Inventors: Kevin P. Campbell, Iowa City; Derrick R. Witcher, Coralville, both of Iowa; Peter McPherson, Branford, Conn.; Steven D. Kahl, Fishers, Ind.; John D. Windass, Wokingham, United Kingdom; Terence Lewis; Philip Bentley, both of Bracknell, United Kingdom

[73] Assignee: University of Iowa Research Foundation, Iowa City, Iowa

[21] Appl. No.: 186,435

[22] Filed: Jan. 25, 1994

[51] Int. Cl.[6] ...................... G01N 33/567; G01N 33/534; C07K 14/76

[52] U.S. Cl. .......................... 436/504; 436/545; 436/822; 530/363; 530/367; 530/380; 530/389.8; 530/404; 530/405

[58] Field of Search ..................................... 530/404, 405, 530/389.8, 363, 367, 380; 436/545, 504, 822; 548/525

[56] References Cited

FOREIGN PATENT DOCUMENTS

WO92/18499 10/1992 WIPO .

OTHER PUBLICATIONS

G. Liu et al., Mol. Pharmacology, vol. 45, No. 2, pp. 189–200 (1994).

J. Gosling, Clin. Chem., vol. 36, No. 8, pp. 1408–1427 (1990).

G. Liu et al., Chem. Abstract No. 120:240990n (1994).

A. Caswell et al., Biochemistry, vol. 30, No. 30, pp. 7507–7513 (1991).

S. Kahl et al., Anal. Biochem., vol. 218, No. 1, pp. 55–62 (1994).

*Primary Examiner*—Mary E. Ceperley
*Attorney, Agent, or Firm*—Kevin M. Farrell

[57] ABSTRACT

Disclosed is a novel photo-activatable derivative of ryanodine 9-hydroxy-21-(4-azidobenzoyloxy)-9-epiryanodine. This novel ryanodine derivative has been conjugated to keyhole limpet hemocyanin (KLH) and used for the production of antibodies with high affinity and specificity to ryanodine. A radioimmunoassay specific for ryanodine was developed using the anti-ryanodine antibodies, and a dissociation constant for ryanodine of 1 nM was determined. Also disclosed is the binding of a labeled, photoactivatable derivative of ryanodine (ABRy) with the ryanodine receptor of skeletal, cardiac and brain membranes. Digestion of the labeled ryanodine receptor revealed a labeled 76 kDa tryptic fragment which is critical for the formation of the high affinity ryanodine binding site.

9 Claims, 10 Drawing Sheets

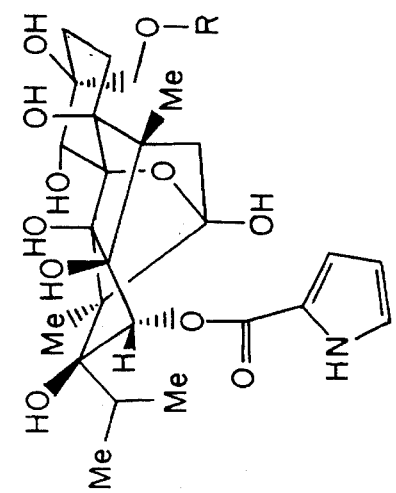
RYANODINE
FIG. 1A
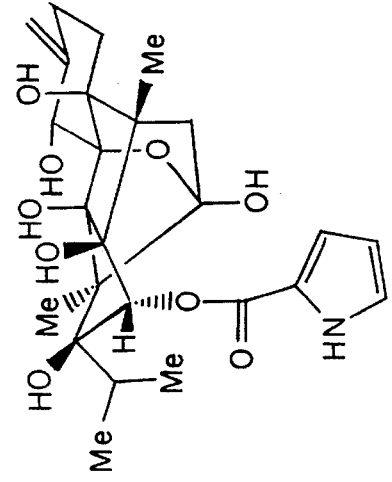
DEHYDRORYANODINE
FIG. 1B
(1) R=H
(2) R=4-N₃-BENZOYL
FIG. 1C
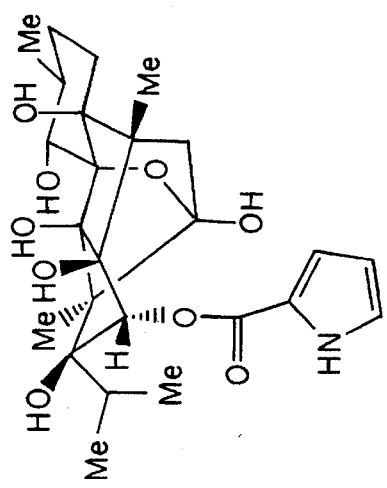
(3) R=H, n=2
(4) R=H, n=4
(5) R=4-N₃-BENZOYL, n=2
(6) R=4-N₃-BENZOYL, n=4
(7) R=CF₃C(N₂)CO-, n=2
FIG. 1D
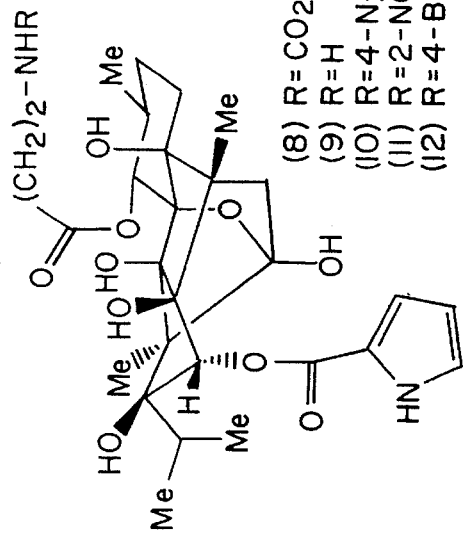
(8) R=CO₂Bn
(9) R=H
(10) R=4-N₃-BENZOYL
(11) R=2-NO₂-5-N₃-BENZOYL
(12) R=4-BENZOYLBENZOYL
FIG. 1E
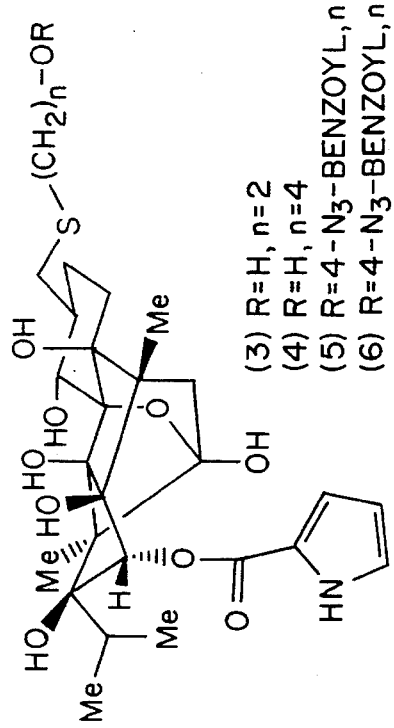

ABRy

RYANODINE

IMMUNOGENIC RYANODINE DERIVATIVE AND RELATED USES

BACKGROUND OF THE INVENTION

Intracellular levels of calcium are regulated by movement of calcium through channels in cellular membranes. Calcium release through an ion channel present in the terminal cisternae of the sarcoplasmic reticulum initiates contraction in skeletal muscle. This $Ca^{2+}$ release channel has been shown to bind the neutral plant alkaloid ryanodine with high affinity and can be regulated by ryanodine, $Ca^{2+}$, ATP, KCl, $Mg^{2+}$ ruthenium red, caffeine and calmodulin.

The use of radiolabeled ryanodine as a probe has led to the identification, purification and biochemical characterization of the $Ca^{2+}$ release channel/ryanodine receptor from skeletal, cardiac and neuronal tissue. The predicted primary structure of the $Ca^{2+}$ release channel/ryanodine receptor has been determined in several species and tissues (see e.g., Takeshima et al., Nature 339, 439–445 (1989); Zorzato et al., *J. Biol. Chem.* 265, 2244–2256 (1990); and Fujii et al., *Science* 253, 448–451 (1991)), but the specific site modulated by ryanodine is unknown.

Ryanodine has different effects on the channel conductance and gating properties depending on the type of tissue and concentration of ryanodine. In skeletal and cardiac muscle for instance, micromolar concentrations of ryanodine inhibit $Ca^{2+}$ release by closing the $Ca^{2+}$ release channel, while nanomolar concentrations of ryanodine stimulate $Ca^{2+}$ release by locking this channel in the open state. In neuronal tissue, micromolar concentrations of ryanodine completely block the channel, however, lower concentrations of ryanodine do not appear to affect the brain $Ca^{2+}$ release channel.

Knowledge about the site of action for ryanodine could provide additional information about receptor structure and function. Since immunologic probes have been widely used for the characterization of membrane proteins and ion channels, one approach toward characterization of the ryanodine binding site involves the production of high-affinity antibodies to ryanodine which mimic the binding characteristics of the skeletal muscle membrane receptor.

Preparation of antibodies to peptides or small molecules like ryanodine (M.W. 493) is usually accomplished by conjugation to a carrier protein for optimal antigenicity. However, derivatization of ryanodine to produce an immunogenic conjugate which retains the essential ryanodine binding properties has proven to be extremely difficult.

SUMMARY OF THE INVENTION

In one aspect, the present invention relates to novel ryanodine derivatives and uses for such derivatives. A conjugates comprising a ryanodine derivative of this invention, linked to an immunogenic protein carrier, has been demonstrated to stimulate the production of antibodies which bind ryanodine with high affinity. Such antibodies are useful in an immunoassay for the detection of ryanodine, or ryanodine-like compounds.

In another aspect, the invention relates to labeled affinity reagents which are useful, for example, in a method for identifying the ryanodine binding site on the ryanodine receptor. Preferred affinity reagents included, for example, 21-(2-[3,3,3-Trifluoro-2-diazopropionyloxy] -ethylmercapto)-ryanodine and 21-(4-Hydroxybutylmercapto)-ryanodine; 10-O-(3-[4-Azidobenzamido]-propionyl)-ryanodine; 10-O-(3-[2-Nitro-5-azidobenzamido]-propionyl)-ryanodine; and 10-O-(3-[4-benzoylbenzamido]-propionyl)-ryanodine.

BRIEF DESCRIPTION OF THE DRAWINGS

FIG. 1 is a diagram representing structures for ryanodine, dehydroryanodine and ryanodine derivatives prepared as described in the Examples which follow.

DETAILED DESCRIPTION OF THE INVENTION

Figure 2:
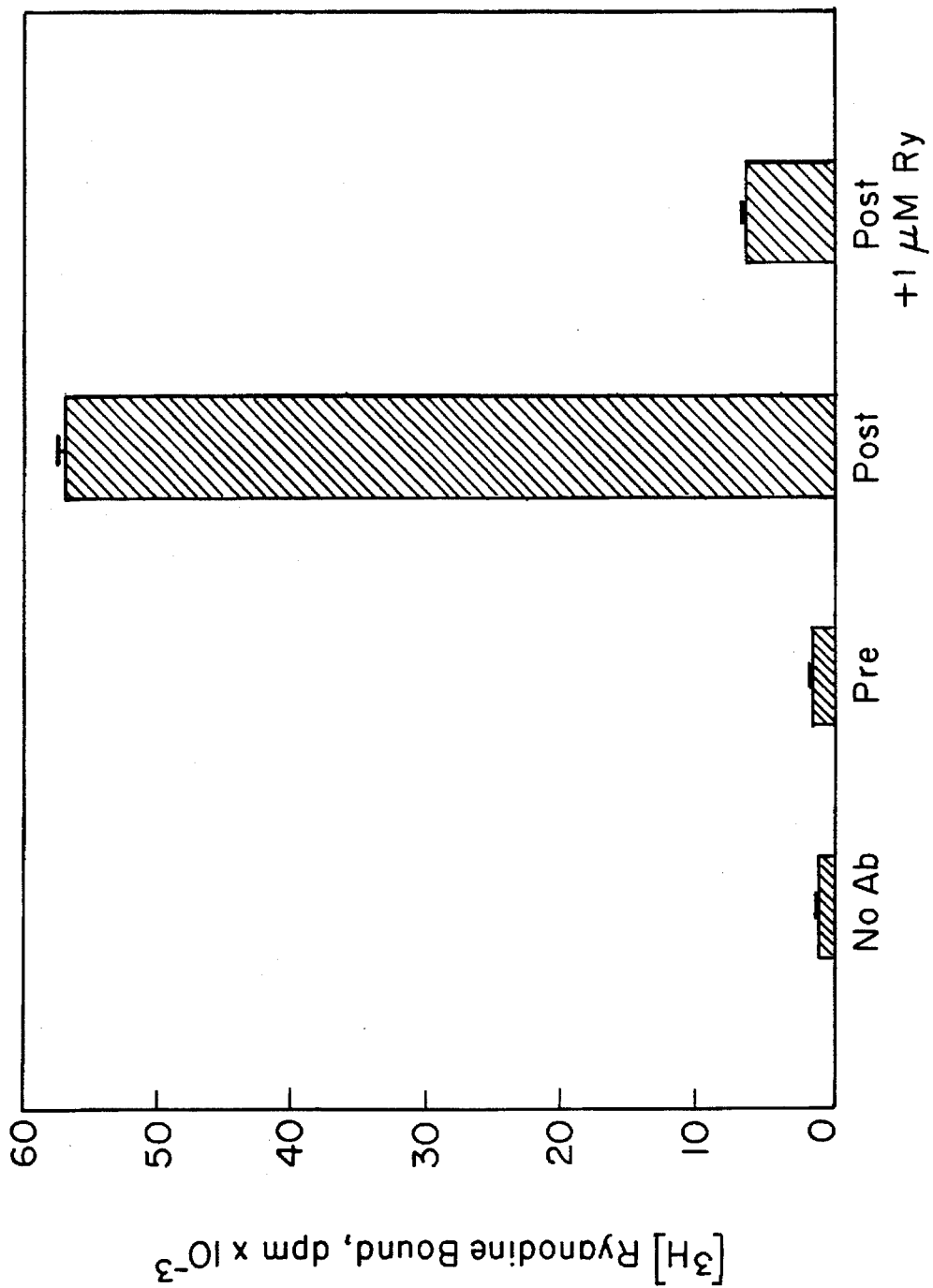
FIG. 2 is a diagram representing results from a dextran-coated charcoal assay which was used to determine the binding characteristics of the anti-ryanodine antibodies. More specifically, 1 nM [$^3$H]ryanodine was added to test tubes containing either no antiserum (No Ab); 10 μl pre-immune serum (Pre), 10 μl post-immune serum (Post); or 10 μl post-immune serum plus 1 mM unlabeled ryanodine (Post+1). Error bars are the SEM for triplicate determinations.

Ryanodine is a naturally occurring compound produced by the *Ryania speciosa* plant which is native to Trinidad. Ryanodine is known to act as an agonist/antagonist of calcium channel activity. This modulating activity requires the specific binding of ryanodine to the ryanodine receptor/calcium release channel which has been extensively studied in both skeletal and cardiac muscle tissue. The ryanodine receptor protein plays a critical role in the regulation of intracellular free calcium concentration which controls muscle contraction. The ryanodine receptor has also been characterized in neuronal tissue, where it is thought to perform a similar role by regulating the intracellular free calcium concentration. The ryanodine receptor/calcium release channel has been isolated from skeletal and cardiac muscle, as well as neuronal tissue, and shown to be a very large homotetramer with a monomer subunit of molecular mass approximately 565 kDa. In addition, ryanodine is known to exhibit potent insecticidal properties and susceptible insects are thought to contain a protein bearing substantial homology to the mammalian ryanodine receptor.

Ryanodine is a hapten, i.e. a molecule which is not sufficiently immunogenic to induce the production of a useful antibody titer when used to immunize a test subject. The conventional approach to stimulating the production antibodies which bind specifically to a hapten is to conjugate the hapten to an immunogenic carrier protein (see, e.g., *Antibodies, A Laboratory Manual*, Harlow ed., Cold Spring Harbor Laboratories, (1988)). However, with the small and highly complex ryanodine molecule, extraordinary experimental effort was required to produce an immunogenic derivative having the ability to stimulate the production of antibodies which bind ryanodine with high affinity.

In one aspect, the present invention is based on the synthesis of such a novel immunogenic ryanodine derivative. An important characteristic of the immunogenic ryanodine derivative is that, following immunization of a mammal, ryanodine-specific antibodies are produced which bind ryanodine with high affinity (e.g., with an $IC_{50}$ of less than $10^{-8}$). As used herein, $IC_{50}$ values refer to half-maximal inhibition determinations of radiolabeled ryanodine for a protein binding partner (e.g., ryanodine receptor or anti-ryanodine antibodies) by ryanodine or ryanodine derivatives.

The chemical structure of the novel immunogenic derivative of ryanodine is shown below wherein R is an immunogenic protein carrier. The immunogenic protein carrier can be any protein or peptide with a preferred molecular weight of at least 4,000. Well known examples of such carriers include bovine serum albumin, casein, ovalbumin or keyhole limpet hemocyanin. The immunogenic protein carrier is conjugated to the ryanodine derivative by conventional methods.

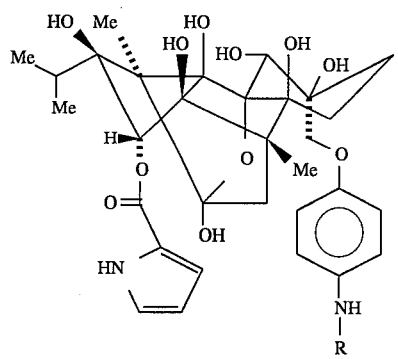

The preparation of the immunogenic derivative of ryanodine, and the characterization of the derivative, are described in detail in the Exemplification section which follows. In addition, the preparation of polyclonal sera from New Zealand White rabbits is also described. Methods for the preparation of polyclonal antisera from other mammalian species is well known in the art. In addition, methods for the production of monoclonal antibodies are well established and the present invention encompasses monoclonal antibodies which bind to ryanodine with the specificity described herein. Such methods for antibody preparation are described, for example, in *Antibodies, A Laboratory Manual*, (Harlow ed., Cold Spring Harbor Laboratories, (1988)). A description of these well-established methodologies will not be re-presented in the present description.

Figure 5:
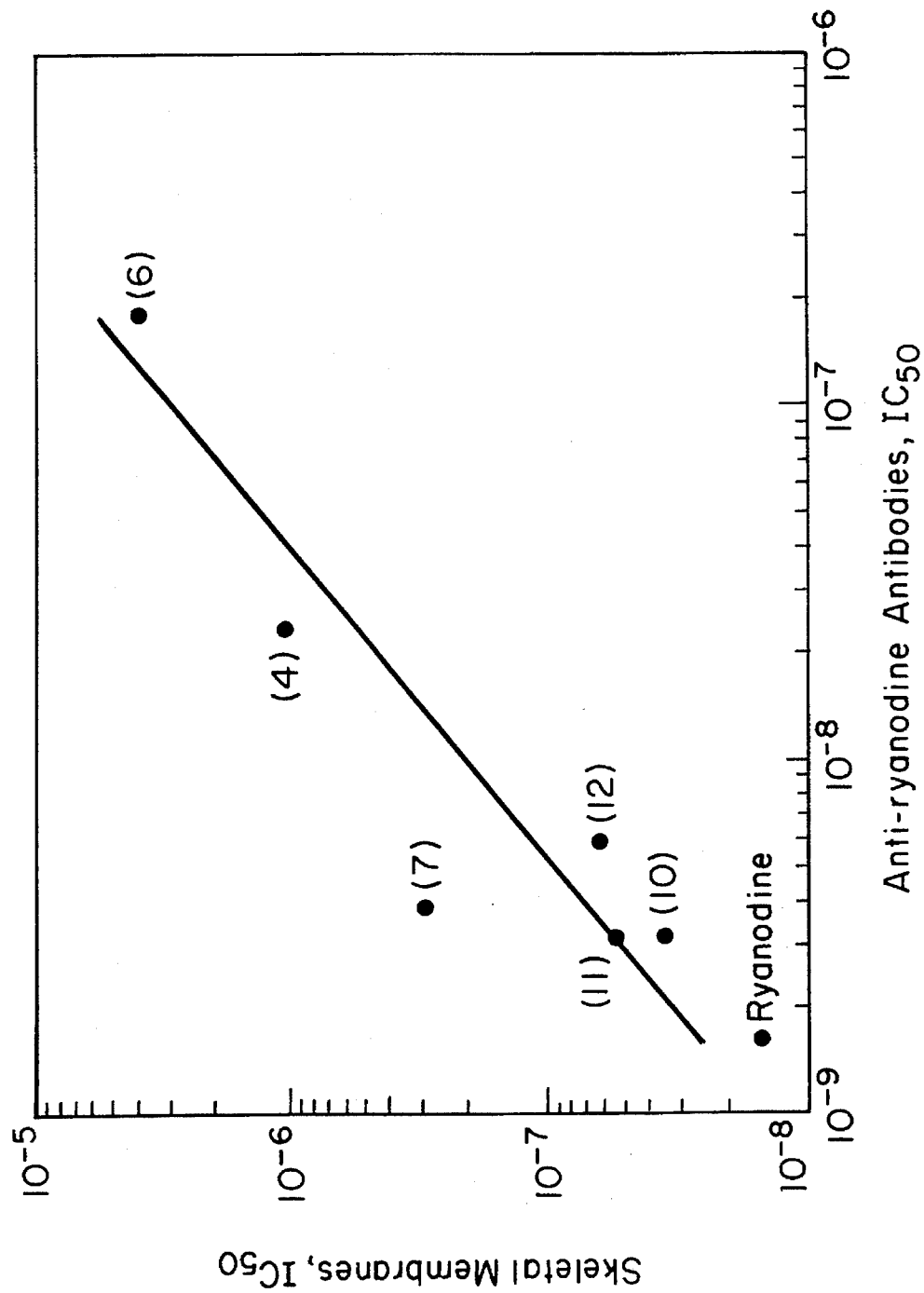
FIG. 5 is a diagram representing a comparison of [$^3$H] ryanodine inhibition to skeletal membranes and anti-ryanodine antibodies. [$^3$H]ryanodine binding to anti-ryanodine antibodies and rabbit skeletal membranes was performed in the presence of various concentrations of unlabeled ryanodine derivatives. In this linear regression comparison, numbers next to data points correspond to the compound numbers from FIG. 1.

Antibodies produced following immunization using the compound described above were tested for binding affinity to ryanodine, as well as to the ryanodine derivatives listed in Table 1 which represent modifications of ryanodine intended for use as affinity labeling reagents (or precursors thereof). In addition, the binding affinity for the compounds listed in Table 1, as well as for ryanodine, to the ryanodine receptor was determined. The results of these experiments are shown, for example, in FIG. 5. A significant observation demonstrated graphically in FIG. 5 is that the antibodies of the invention bind ryanodine with very high affinity. More specifically, the antibodies of the invention were determined to bind ryanodine with an $IC_{50}$ of less than $10^{-8}$.

TABLE 1

Inhibition of [$^3$H] ryanodine-antibody binding by ryanodine and ryanodine derivatives

| Compound | | $IC_{50}$, nM |
|---|---|---|
| Ryanodine | | 1.6 |
| Ryanodine Derivatives | | |
| 21-(2-[3,3,3-Trifluoro-2-diazopropionyloxy]-ethylmercapto)-ryanodine | 7* | 4 |
| 21-(4-Hydroxybutylmercapto)-ryanodine | 4* | 25 |
| 21-(2-[4-Azidobenzoyloxy]-butylmercapto)-ryanodine | 6* | 198 |
| 10-O-(3-[4-Azidobenzamido]-propionyl)-ryanodine | 10* | 3.2 |
| 10-O-(3-[2-Nitro-5-azidobenzamido]-propionyl)-ryanodine | 11* | 3.2 |
| 10-O-(3-[4-benzoylbenzamido]-propionyl)-ryanodine | 12* | 6 |

Numbers indicated by * correspond to compound numbers in FIG. 1.

An additional unanticipated result, demonstrated in the Exemplification section below and shown graphically in FIG. 5, relates to the fact that the affinity of the novel compounds disclosed in Table 1 for the ryanodine receptor is remarkably mimicked by their affinity for the anti-ryanodine antibodies of this invention. More specifically, the $IC_{50}$ values reported, for Example in FIG. 5, show that Compound 6 binds with relatively low affinity (substantially greater than $10^{-7}$) to both the ryanodine receptor and to the antibodies of this invention. This result indicates that the antibodies are interacting chemically with the ryanodine derivative in a manner which is highly analogous to the manner in which the ryanodine derivative interacts with the ryanodine receptor. Similar high affinity binding characteristics were observed with Compounds 4 and 7 ($IC_{50}$ of less than about $10^{-6}$) and Compounds 10, 11 and 12 ($IC_{50}$ of less than about $10^{-7}$).

Furthermore, Compounds 10, 11 and 12 exhibited a binding affinity for both the ryanodine receptor and the anti-ryanodine antibodies which very nearly matched the affinity of native ryanodine for its receptor and for the antibodies of this invention. This result evidences the strong structural similarity of the antibody variable region and the ryanodine binding site of the naturally occurring ryanodine receptor.

This similarity in the ryanodine binding characteristics of the antibody and the naturally occurring ryanodine receptor establishes the utility of the antibodies of this invention as an affinity reagent for use in screening for compounds sharing structural, and therefore, functional similarity with ryanodine. Such an affinity reagent enables a high-throughput screening assay in which thousand of compounds can be rapidly screened. Antibodies having the specificity described in the present invention can be incubated with a solution containing small organic molecules to be tested for ryanodine-like binding properties. For example, extracts from plant and fungal sources provide useful solutions to be screened for the presence of such compounds. In addition, synthetic derivatives of ryanodine, or ryanodine-like compounds can be screened in this manner. Furthermore, biological fluids such as serum, urine and cerebrospinal fluid can be screened for ryanodine-like compounds. As used herein, the term "ryanodine-like" compounds are defined as compounds which bind specifically to the antibodies of this invention. Preferably, the ryanodine-like compounds bind the antibodies of this invention with an $IC_{50}$ of less than about $10^{-6}$. Such compounds represent candidate agonist/antagonist compounds which can be subsequently tested for the ability to modulate calcium channel activity. In addition, such compounds represent candidate insecticidal compounds which can be subsequently tested in an appropriate assay for such activity.

Additional uses for the antibodies of the invention include, for example, the detection of ryanodine or ryanodine-like compounds in an antibody-based binding assay. Ryanodine, or ryanodine-like compounds, may be used clinically to modulate calcium channel activity, for example, in the treatment of a variety of cardiovascular, neuromuscular and neurological disorders which are known to be characterized by irregularity in intracellular calcium concentrations. If ryanodine or derivatives thereof are to be used in this manner, the ability to accurately monitor serum levels of ryanodine will be extremely important. As discussed in the Background of the Invention section, variability in serum levels can have a profound effect (including reversal of the desired effect) on the calcium channel activity. The antibodies of the present invention have been used to develop a sensitive immunoassay which facilitates the determination of ryanodine levels in a sample. In addition, the antibodies of the present invention could be used as a clinical reagent to prevent, or reverse, ryanodine intoxication. More specifically, if it is determined that serum levels of ryanodine are unacceptably high, antibodies can be administered in an appropriate formulation. The administered antibodies will complex with ryanodine, thereby dramatically increasing the rate of clearance of ryanodine from the serum.

Any conventional assay format which relies on a single antibody specificity is appropriate. In a preferred assay format, the sample to be tested is a liquid sample which is suitable for protein binding studies. It is not possible to define a priori the characteristics of all liquid samples which fall within this category. However, using only routine experimentation, one of skill in the art can determine whether a particular liquid sample provides an environment suitable for protein binding studies. Among the biological fluids which provide a suitable environment for protein binding studies are serum, urine and cerebrospinal fluid.

A fixed amount of radiolabeled ryanodine and antibody which binds specifically to ryanodine is then added to the solution. Preferably, the antibody is characterized by the ability to bind ryanodine with an $IC_{50}$ of less than $10^{-8}$. The reaction mixture is then incubated under conditions appropriate for the specific binding of ryanodine to the labeled antibody. The ryanodine/antibody complex is then separated from the unbound ryanodine by conventional techniques (e.g., immunoprecipitation) and the radioactive content of either the complex or the unbound ryanodine is determined.

In another aspect, the invention relates to a kit for conducting immunoassays of the type described above. Such a kit would include, for example, radiolabeled ryanodine, an antibody which binds to ryanodine, and serial dilutions of ryanodine standard solutions.

Also disclosed herein are affinity labeling reagents which are useful, for example, in a method for the identification of the ryanodine binding site in the ryanodine receptor. Such information is useful, for example, in the design and screening of compounds which mimic the binding characteristics of ryanodine.

More specifically, FIG. 5 provides data demonstrating the identification of ryanodine derivatives which bind to the ryanodine receptor with high affinity, and some of which are derivitized in a manner which facilitates their use as affinity labeling reagents. The structures of each of the compounds whose binding characteristics is reported in FIG. 5 are shown in FIG. 1. Many of the compounds have been derivitized in such a manner that a photoactivated linkage is formed between it, and any protein with which it is tightly associated, following exposure to UV light.

Photoaffinity labeling provides a powerful tool for studying ligand binding sites on their receptors (e.g., ryanodine binding to the ryanodine receptor). With the use of radiolabeled photoactivatable compounds, it is possible to define and identify the portion of the receptor which specifically binds the compound. Identification of the ligand binding site will then make it possible to design models of this binding site which show predicted secondary and tertiary structure. Such modeling techniques are well known in the art and information gained from such studies is useful in the production of compounds which bind more specifically (or with higher affinity) to the ligand binding site.

As described in detail in Example 2, following activation of a photoactivatable derivatives of ryanodine which results in cross-linking to any tightly associated protein, the associated protein is subjected to digestion (e.g., endoproteolytic enzymatic digestion). Fragments of such a digestion are then analyzed to determine which fragment is cross-linked to the photoactivated ryanodine derivative. To facilitate detection, the affinity reagent is labeled by standard techniques, for example, with a radiolabel such as $^3$H or $^{125}$I. Information gained through such experiments is useful for identification of the site of ryanodine interaction on the ryanodine receptor.

The preferred affinity labeling reagents of this invention are 21-(2-[3,3,3-Trifluoro-2-diazopropionyloxy]-ethylmercapto)-ryanodine and 21-(4-Hydroxybutylmercapto)-ryanodine (which binds to the ryanodine receptor with an $IC_{50}$ of less than about $10^{-6}$) and 10-O-(3-[4-Azidobenzamido]-propionyl)-ryanodine; 10-O-(3-[2-Nitro-5-azidobenzamido]-propionyl)-ryanodine; and 10-O-(3-[4-benzoylbenzamido]-propionyl)-ryanodine (which bind to the ryanodine receptor with an $IC_{50}$ of less than about $10^{-7}$).

EXAMPLE 1

Abbreviations

BSA, bovine serum albumin; KLH, keyhole limpet hemocyanin; PBS, phosphate buffered saline; SDS-PAGE, sodium dodecyl sulphate polyacrylamide gel electrophoresis; BLOTTO, bovine lacto transfer technique optimizer; TSG, tris/saline/gelatin; $IC_{50}$, inhibition constant at 50% binding; and azido-ryanodine, 9-hydroxy-21-(4-azidobenzoyloxy)-9-epiryanodine.

Materials

[$^3$H]Ryanodine (61.5 Ci/mmol) was obtained from New England Nuclear. Ryanodine used in biochemical studies was obtained from Penick (Lyndhurst, N.J.). Ryanodine and dehydroryanodine used in synthesis were obtained as an approximately 1:1 mixture from Agra Systems International (Windgap, Pa.) and separated by reverse phase HPLC. Dextran T-70 was obtained from Sigma and Norit A was obtained from Fisher Scientific. Bovine serum albumin and keyhole limpet hemocyanin were from Pierce Chemical Co. Gelatin was obtained from Bio-Rad and electrophoresis reagents and secondary antibodies were from Boehringer Mannheim. All other reagents were of reagent grade quality.

Preparation of Compounds

Tetrahydrofuran (THF) was dried by distillation from sodium and benzophenone and stored over 4A molecular sieves under nitrogen. HPLC separations were carried out using a Gilson 303 system and a Spherisorb S5 ODS2 column. The flow rate was 10 ml/min and detection was carried out at 268 nm. Nmr spectra were recorded on a JEOL GSX 270 spectrometer. Mass spectra were determined by fast atom bombardment ionization (FAB) using a JEOL JMX-DX 303 instrument.

9,21-Dihydroxy-9-epiryanodine (1).

Dehydroryanodine (50 mg, 102 μM) was added to a solution of osmium trichloride (4 mg, 24 μM) and N-methylmorpholine (30 mg, 240 μM) in 50% aqueous THF (2 ml). The mixture was stirred at room temperature for 24 hours. The reaction was quenched by adding saturated aqueous solutions of $NaHSO_3$ (2 ml) and $NaHCO_3$ (2 ml), and then evaporated to dryness. The residue was extracted with a mixture of methanol and chloroform (1:3, 10 ml) and, after filtration, the solution was passed through a short silica column which was then eluted with more solvent. Evaporation of the resulting solution gave the crude product (95 mg). The product was purified on reverse phase HPLC using aqueous methanol (55:45) as the mobile phase ($t_R$=12.5 min) to give 51 mg (95%) of pure material, identical with that reported previously (Waterhouse et al., J. Med. Chem. 30: 660–666 (1983)), FAB ms m/e: 526 (MH$^+$).

9-Hydroxy-21-(4-azidobenzoyloxy)-9-epiryanodine (2).

Compound 1 (70 mg, 133 μM) was dissolved in dry THF and to this solution at room temperature was added 4-azidobenzoyl chloride (27 mg, 150 μM) and dry pyridine (12 mg). The mixture was stirred in subdued light for 5 days and then evaporated under reduced pressure. The resulting residue was taken up in aqueous methanol (3:7 2 ml) and passed down a short reverse phase column, which was further eluted with the same solvent. The eluent was evaporated under reduced pressure to give the crude product (105 mg). The product was purified by twice passing it through a reverse phase HPLC column in aqueous methanol (3:7) to give 35 mg (39%) of 2 ($t_R$=13.5 min). ir (90% CHCl$_3$, 10% MeOH) 2118 cm$^{-1}$ (N$_3$).

$^1$H nmr (CD$_3$OD, δ ppm): 8.03 (d, 2H, J=7 Hz), 7.08 (d, 2H, J=7 Hz), 6.96 (m, 1H), 6.79 (m, 1H), 6.16 (m, 1H), 5.56 (s, 1H), 4.95 (d, 1H, J=12 Hz), 4.49 (d, 1H, J=12 Hz), 4.36 (s, 1H), 2.51 (d, 1H, J=14 Hz), 2.19 (sept, 1H, J=6 Hz), 2.06 (dt, 1H, J=6, 14 Hz), 1.96 (m, 1H), 1.85 (d, 1H, J=14 Hz), 1.82 (m, 1H), 1.36 (s, 3H), 1.25 (m, 1H), 1.04 (d, 3H, J=6 Hz), 0.84 (s, 3H), 0.67 (d, 3H, J=6 Hz). FAB ms m/e: 671 (MH$^+$).

21-(2-Hydroxyethylmercapto)-ryanodine (3).

Dehydroryanodine (100 mg, 204 μM) and 2-mercaptoethanol (100 mg, 1280 μM) were dissolved in dry THF (5 ml), together with catalytic amounts of AIBN (10 mg) and tributyltin oxide (14 mg). The mixture was stirred at room temperature for 7 days and then evaporated to dryness under reduced pressure. The residue was dissolved in aqueous methanol (55:45, 2 ml) and filtered through a short column of silica, which was then washed with aqueous methanol (10 ml). The total solution was evaporated to dryness to give the crude product (115 mg). This material was then purified by reverse phase HPLC using aqueous methanol (55:45) to give 85 mg (73%) of pure product 3 ($t_R$=25 min).

$^1$H nmr (CD$_3$OD, δ ppm): 6.96 (m, 1H), 6.79 (m, 1H), 6.15 (m, 1H), 5.56 (s, 1H), 3.95 (d, 1H, J=10 Hz), 3.60 (t, 2H, J=7 Hz), 2.94 (m, 1H), 2.58 (dt, 2H, J=2.7 Hz), 2.50 (d, 1H, J=14 Hz), 2.36 (m, 1H), 2.21 (sept, 1H, J=6 Hz), 2.01 (m, 1H), 1.89 (m, 1H), 1.87 (d, 1H, J=14 Hz), 1.76 (m, 1H), 1.45 (m, 1H), 1.32 (s, 3H), 1.24 (m, 1H), 1.05 (d, 3H, J=6 Hz), 0.83 (s, 3H), 0.67 (d, 3H, J=6 Hz). FAB ms m/e: 570 (MH$^+$).

21-(4-Hydroxybutylmercapto)-ryanodine (4).

This compound was made in 19% yield by a route similar to that for 3, from dehydroryanodine (50 mg) and 4-mercaptobutanol (50 mg). On reverse phase HPLC (40:60 aqueous methanol) $t_R$=10.5 minutes.

$^1$H nmr (CD$_3$OD, δ ppm): 6.96 (m, 1H), 6.79 (m, 1H), 6.16 (m, 1H), 5.56 (s, 1H), 3.90 (d, 1H, J=10 Hz), 3.50 (t, 2H, J=7 Hz), 2.93 (m, 1H), 2.49 (d, 1H, J=14 Hz), 2.47 (m, 2H), 2.31 (m, 1H), 2.19 (sept, 1H, J=6 Hz), 2.0 (m, 1H), 1.93 (m, 1H), 1.85 (d, 1H, J=14 Hz), 1.75 (m, 1H), 1.56 (m, 4H), 1.44 (m, 1H), 1.31 (s, 1H), 1.23 (m, 1H), 1.03 (d, 3H, J=6 Hz), 0.81 (s, 3H), 0.67 (d, 3H, J=6 Hz).

21-(2-[4-Azidobenzoyloxy]-ethylmercapto)-ryanodine (5).

Compound 3 (8 mg, 14 μM) was dissolved in dry THF (1 ml). To this was added 4-azidobenzoic acid (4.5 mg, 28 μM) and dicyclohexylcarbodiimide (DCC; 6 mg, 28 μM) and DMAP (1 mg). The mixture was then stirred in subdued light at room temperature for 4 days. The reaction mixture was evaporated under reduced pressure and the residue dissolved in aqueous methanol (3:7) and passed down a short reverse phase column. The eluent was evaporated to leave the crude product (22 mg). This material was purified twice by reverse phase HPLC, with aqueous methanol (32:68) as the mobile phase ($t_R$=26 min). The pure product 5, 7.5 mg (75%), was then obtained.

$^1$H nmr (CD$_3$OD, δ ppm): 7.98 (d, 2H, J=7 Hz), 7.10 (d, 2H, J=7 Hz), 6.96 (m, 1H), 6.79 (m, 1H), 6.15 (m, 1H), 5.56

(s, 1H), 4.36 (t, 2H, J=7 Hz), 3.99 (d, 1H, J=10 Hz), 3.03 (m, 1H), 2.83 (dt, 2H, J=2, 7 Hz), 2.50 (d, 1H, J=14 Hz), 2.43 (m, 1H), 2.19 (sept, 1H, J=6 Hz), 2.01 (m, 1H), 1.89 (m, 1H), 1.87 (d, 1H, J=14 Hz), 1.76 (m, 1H), 1.46 (m, 1H), 1.32 (s, 3H), 1.24 (m, 1H), 1.05 (d, 3H, J=6 Hz), 0.83 (s, 3H), 0.67 (d, 3H, J=6 Hz).

21-(2-[4-Azidobenzoyloxy]-butylmercapto)-ryanodine (6).

By an analogous route to that above 6 was made in 40% yield from compound 4 (8 mg, 14 μM). It was purified by reverse phase HPLC (aqueous methanol 25:75, $t_R$=17 min).

$^1$H nmr (CD$_3$OD, δ ppm): 7.97 (d, 2H, J=8 Hz), 7.10 (d, 2H, J=8 Hz), 6.95 (m, 1H), 6.79 (m, 1H), 6.17 (m, 1H), 5.56 (s, 1H), 4.25 (t, 2H, J=7 Hz), 3.92 (d, 1H, J=10 Hz), 2.91 (m, 1H), 2.52 (m, 2H), 2.48 (d, 1H, J=14 Hz), 2.33 (m, 1H), 2.19 (sept, 1H, J=16 Hz), 1.99 (m, 1H), 1.92 (m, 1H), 1.85 (d, 1H, J=14 Hz), 1.84–1.6, m, 5H), 1.44 (m, 1H), 1.32 (s, 3H), 1.22 (m, 1H), 1.03 (d, 3H, J=6 Hz), 0.83 (s, 3H), 0.67 (d, 3H, J=6 Hz).

21-(2-[3,3,3-Trifluoro-2-diazopropionyloxy]-ethylmercapto)-ryanodine (7).

Compound 3 (20 mg, 40 μM) was dissolved in dry THF (1.5 ml). To this was added pyridine (8 mg, 100 μM) and 3,3,3-trifluoro-2-diazopropionyl chloride (14 mg, 80 μM) and the mixture was stirred in subdued light for 7 days at room temperature. The solution was then evaporated under reduced pressure to give the crude product (41 mg) which was purified twice by reverse phase HPLC ($t_R$=11 min) using aqueous methanol 28:72 as the mobile phase, which had been pre-adjusted to pH 7.6 with triethylamine to limit decomposition of the product. The product (4 mg, 16%) showed the following spectral characteristics: $^{19}$F (CD$_3$OD, $\delta_{FCCl3}$)–57.5 ppm.

$^1$H nmr (CD$_3$OD, δ ppm): 7.96 (m, 1H,), 6.81 (m, 1H), 6.16 (m, 1H), 5.56 (s, 1H), 4.33 (t, 2H, J=7 Hz), 3.93 (d, 1H, J=10 Hz), 3.00 (m, 1H), 2.75 (dt, 2H, J=2, 7 Hz), 2.50 (d, 1H, J=14 Hz), 2.39, (m, 1H), 2.19 (sept, 1H, J=6 Hz), 2.02 (m, 1H), 1.92 (m, 1H), 1.86 (d, 1H, J=14 Hz), 1.72 (m, 1H), 1.43 (m, 1H), 1.31 (s, 3H), 1.22 (m, 1H), 1.03 (d, 3H, J=6 Hz), 0.81 (s, 3H,), 0.69 (d, 3H, J=6 Hz). FAB ms m/e: 728 (MNa$^+$).

10-O-(3-Benzyloxycarbamoyl-propionyl)-ryanodine (8).

Ryanodine (540 mg, 1.1 mM) was dissolved in dry THF (20 ml) followed by 3-benzyloxycarbamoyl-propionic acid (260 mg, 1.17 mM), DCC (1 g, 4.85 mM) and a catalytic amount of DMAP (20 mg). After stirring for 18 hours further amounts of DCC (500 mg) and the propionic acid derivative (130 mg) were introduced and stirring was continued for a further 24 hours. The solution was then evaporated to dryness and the remainder was suspended in 50% aqueous methanol (30 ml), filtered and the filtrate was evaporated under reduced pressure. The crude product was then resuspended in a smaller volume of 50% aqueous methanol (10 ml) from which an oil separated (280 mg). The oil was chromatographed on silica (5% methanol in chloroform as the mobile phase) and then twice on reverse phase HPLC, in aqueous methanol (35:65, $t_R$=16.5 min) to give e (53 mg, 7%).

$^1$H nmr (CD$_3$OD, δ ppm): 7.33–7.18 (m, 5H), 6.97 (m, 1H), 6.80 (m, 1H), 6.17 (m, 1H), 5.51 (s, 1H), 5.25 (d, 1H, J=10 Hz), 5.04 (d, 1H, J=12 Hz), 4.97 (d, 1H, J=12 Hz), 3.37 (t, 2H, J=6 Hz), 2.53 (t, 2H, J=6 Hz), 2.51 (d, 1H, J=14 Hz), 2.19 (sept, 1H, J=6 Hz), 2.15–1.90 (m, 2H), 1.88 (d, 1H, J=14 Hz), 1.56–1.40 (m, 2H), 1.31 (s, 3H), 1.24 (m, 1H), 1.03 (d, 3H, J=6 Hz), 0.83 (s, 3H), 0.76 (d, 3H, J=6 Hz), 0.68 (d, 3H, J=6 Hz).

10-O-(3-Aminopropionyl)-ryanodine (9).

Compound 8 (23 mg, 33 μM) was dissolved in methanol, a palladium catalyst (5% Pd on charcoal; 2 mg) was added and the mixture was hydrogenated under a 2 bar pressure of hydrogen for 1.5 hours. The reaction mixture was filtered through hi-flo and the filtrate evaporated under reduced pressure to give the product (19.5 mg). This material showed a single spot on TLC ($R_f$=0.1 on SiO$_2$ using CHCl$_3$:MeOH:40% aq.MeNH$_2$=85:15:2) and was not purified further.

$^1$H nmr (CD$_3$OD, δ ppm): 6.96 (m, 1H), 6.79 (m, 1H), 6.16 (m, 1H), 5.50 (s, 1H), 5.24 (m, 1H), 2.85 (t, 2H, J=6 Hz), 2.49 (d, 1H, J=14 Hz), 2.47 (t, 2H, J=6 Hz), 2.18 (sept, 1H, J=6 Hz), 2.15–1.90 (m, 2H), 1.87 (d, 1H, J=14 Hz), 1.56–1.40 (m, 2H), 1.33 (s, 3H), 1.23 (m, 1H), 1.03 (d, 3H, J=6 Hz), 0.82 (s, 3H), 0.77 (d, 3H, J=6 Hz), 0.67 (d, 3H, J=6 Hz).

10-O-(3-[4-Azidobenzamido]-propionyl)-ryanodine (10).

Compound 9 (7 mg, 12.4 μM) in THF (1 ml) was reacted at 20° with 4-azidobenzoic acid (4.5 mg, 27 μM) and a solution of 1-(3-dimethylaminopropyl)-3-ethylcarbodiimide hydrochloride (18 mg, 94 μM) in dichloromethane (1 ml). After stirring in subdued light for 1 hour the mixture was evaporated to dryness and the residue was purified by chromatography first on a silica column (in 85% CHCl$_3$ 15% MeOH) and then on a reverse phase HPLC column using aqueous methanol (35:65, $t_R$=19 min) to give 10 (5.5 mg, 63%).

$^1$H nmr (CD$_3$OD, δ ppm): 7.78 (d, 2H, J=8 Hz), 7.06 (d, 2H, J=8 Hz), 6.95 (m, 1H), 6.78 (m, 1H), 6.15 (m, 1H), 5.48 (s, 1H), 5.25 (d, 1H, J=10 Hz), 3.60 (m, 2H), 2.64 (t, 2H, J=6 Hz), 2.50 (d, 1H, J=14 Hz), 2.18 (sept, 1H, J=6 Hz), 2.13–1.89 (m, 2H), 1.87 (d, 1H, J=14 Hz), 1.54–1.40 (m, 3H), 1.31 (s, 3H), 1.24 (m, 1H), 1.02 (d, 3H, J=6 Hz), 0.83 (s, 3H), 0.76 (d, 3H, J=6 Hz), 0.64 (d, 3H, J=6 Hz).

10-O-(3-[2-Nitro-5-azidobenzamido]-propionyl)-ryanodine (11).

This compound was made by a method similar to that for 10, using 2-nitro-5-azidobenzoic acid. The product (5 mg, 53%) on HPLC had a $t_R$=12 minutes.

$^1$H nmr (CD$_3$OD, δ ppm): 8.09 (d, 1H, J=9 Hz), 7.24 (dd, 1H, J=3, 9 Hz), 7.11 (d, 1H, J=3 Hz), 6.96 (m, 1H), 6.78 (m, 1H), 6.15 (m, 1H), 5.50 (s, 1H), 5.23 (d, 1H, J=10 Hz), 3.59 (t, 2H, J=6 Hz), 2.67 (t, 2H, J=6 Hz), 2.49 (d, 1H, J=14 Hz), 2.15 (sept, 1H, J=6 Hz), 2.14–1.78 (m, 2H), 1.86 (d, 1H, J=14 Hz), 1.53–1.4 (m, 2H), 1.32 (s, 3H), 1.21 (m, 1H), 1.03 (d, 3H, J=6 Hz), 0.81 (s, 3H), 0.77 (d, 3H, J=6 Hz), 0.65 (d, 3H, J=6 Hz).

10-O-(3-[4-benzoylbenzamido]-propionyl)-ryanodine (12).

Using 4-benzoylbenzoic acid and a method similar to that for 10, the product 12 (4 mg, 42%) was obtained. On HPLC it had a $t_R$=18 minutes.

$^1$H nmr (CD$_3$OD, δ ppm): 7.89 (d, 2H, J=8 Hz), 7.73 (m, 4H), 7.57 (m, 1H), 7.47 (m, 2H), 6.96 (m, 1H), 6.79 (m, 1H), 6.16 (m, 1H), 5.47 (s, 1H), 5.26 (d, 1H, J=10 Hz), 3.65 (m, 2H), 2.69 (m, 2H), 2.49 (d, 1H, J=14 Hz), 2.15 (sept, 1H, J=6 Hz), 2.14–1.86 (m, 2H), 1.85 (d, 1H, J=14 Hz), 1.57–1.39 (m, 2H), 1.29 (s, 3H), 1.23 (m, 1H), 1.00 (d, 3H, J=6 Hz), 0.82 (s, 3H), 0.75 (d, 3H, J=6 Hz), 0.63 (d, 3H, J=6 Hz).

Preparation of Immunogenic Azido-Ryanodine Derivative

The synthesis of the compound 9-hydroxy-21-(4-azidobenzoyloxy)-9-epiryanodine (Compound (2), FIG. 1) provided an analog of ryanodine with an added azido group which could be activated by UV light for attachment to carrier proteins (such as KLH or BSA) via available amines. Compound 2 was covalently coupled to the carrier proteins KLH and BSA for antibody production and analysis of antiserum. More specifically, lyophilized carrier protein (5 mg) was dissolved in 0.5 ml sterile filtered H$_2$O and 6 mg azido-ryanodine was dissolved in 0.5 ml 50% ethanol. The carrier protein was added to 2 ml PBS, pH 7.4, mixed and combined with the dissolved azido-ryanodine in a 30 mm diameter plastic disposable petri dish. The mixture was irradiated in the petri dish for 30 min at 4° C. using a Spectroline Model ENF-280C handheld ultraviolet lamp at 365 nm. Following irradiation, the carrier protein-ryanodine conjugates were aliquoted and stored at −20° C. All steps, prior to UV irradiation, in the preparation of the carrier protein-ryanodine conjugate were performed in dim or indirect lighting.

Immunization and Production of Anti-Ryanodine Antibodies

Female New Zealand white rabbits were bled on Day 0 prior to injection to obtain preimmune sera. The rabbits received 0.9 mg of KLH-ryanodine conjugate (based on KLH concentration in the mixture) emulsified in Freund's complete adjuvant at multiple subcutaneous and intramuscular sites. Subsequent injections of 0.1 to 0.5 mg of KLH-ryanodine conjugate were emulsified in Freund's incomplete adjuvant and administered at 2–3 week intervals. Rabbits were bled one week after the second injection and again one week following each boost. Blood was collected from the outer marginal ear vein, allowed to clot at 25° C. for 15 min and stored at 4° C. for 1–2 hours. Serum was removed following centrifugation for 20 min at 10,000 rpm in a Beckman JA-17 rotor and stored frozen at −20° C.

Immunoblot Analysis of Anti-Ryanodine Antibodies

BSA or BSA-ryanodine conjugate (1 µg each) was separated by 3–12% SDS-PAGE and transferred to nitrocellulose as previously described (Ohlendieck et al., Neuron 7, 499–508 (1991)). Immunoblots were blocked with PBS-BLOTTO (PBS-5% non-fat dried milk) for 1 h and incubated overnight on a rocker at room temperature with anti-ryanodine antibodies at a 1:100 dilution. The nitrocellulose membranes were washed twice for 10 min and then incubated for 1 h with a 1:1000 dilution of horseradish peroxidase-linked goat anti-rabbit secondary antibody. The membranes were then washed twice for 10 min and developed using 4-chloro-1-naphthol as substrate. All washes and incubations were performed using PBS-BLOTTO.

Postimmune serum reacted positively with BSA-ryanodine conjugate, but not with BSA alone. There was no reaction on an identical blot when stained with preimmune serum. Furthermore, when a similar blot was incubated with postimmune serum in the presence of 1 µM unlabeled ryanodine, the reaction with the immobilized BSA-ryanodine conjugate was abolished.

[$^3$H]Ryanodine Binding—Dextran-coated Charcoal Assay

[$^3$H]Ryanodine binding characteristics of the isolated anti-ryanodine antibodies were determined using a dextran-coated charcoal assay similar to an assay developed for the 1,4-dihydropyridine calcium channel blockers (Campbell et al., Proc. Natl. Acad. Sci. U.S.A. 83, 2792–2796 (1986); and Campbell et al., J. Cardiovasc. Pharmacol. 9(Suppl. 4), S113–S121 (1987)). This assay was used because the dextran-coated charcoal is able to precipitate free [$^3$H]ryanodine but not [$^3$H]ryanodine that is bound to the anti-ryanodine antibodies. Binding was performed in triplicate in 1.5 ml polypropylene tubes. Each assay tube contained 1 ml of TSG (Tris/Saline/Gelatin consisting of 150 mM NaCl, 10 mM Tris, pH 7.2 and 0.1% gelatin) and a final concentration of 1 nM [$^3$H]ryanodine. Following the addition of serial dilutions of antibody, the tubes were shaken and incubated for 1 h at room temperature. The tubes were placed on ice for 10 min and then 0.2 ml of stirred, ice-cold dextran-coated charcoal (0.0625% Dextran T-70, 0.625% Norit A charcoal in TSG) was added to each tube. The tubes were shaken and incubated for an additional 10 min on ice. The charcoal was removed by centrifugation (850×g) for 15 min in a Beckman TJ-6R centrifuge and [$^3$H]ryanodine binding was measured by counting 0.5 ml of the supernatant in a liquid scintillation counter. Controls without antiserum were included to determine the amount of radiolabel that could not be precipitated by the charcoal. These values were subtracted from values obtained for the antiserum to determine the total specific [$^3$H]ryanodine bound to the antibody.

In a typical assay, the anti-ryanodine antibodies bound greater than 95% of the added [$^3$H]ryanodine and were specifically inhibited by 1 µM unlabeled ryanodine (FIG. 2). In addition, the precipitation of [$^3$H]ryanodine in the absence of added antibody or in the presence of preimmune antiserum only were at background levels (less than 2% of total binding). Similar assays were performed using anti-ryanodine antibodies immobilized on protein A-Sepharose with identical binding results. These assays demonstrate the specific interaction of the anti-ryanodine antibodies with [$^3$H]ryanodine.

Figure 3:
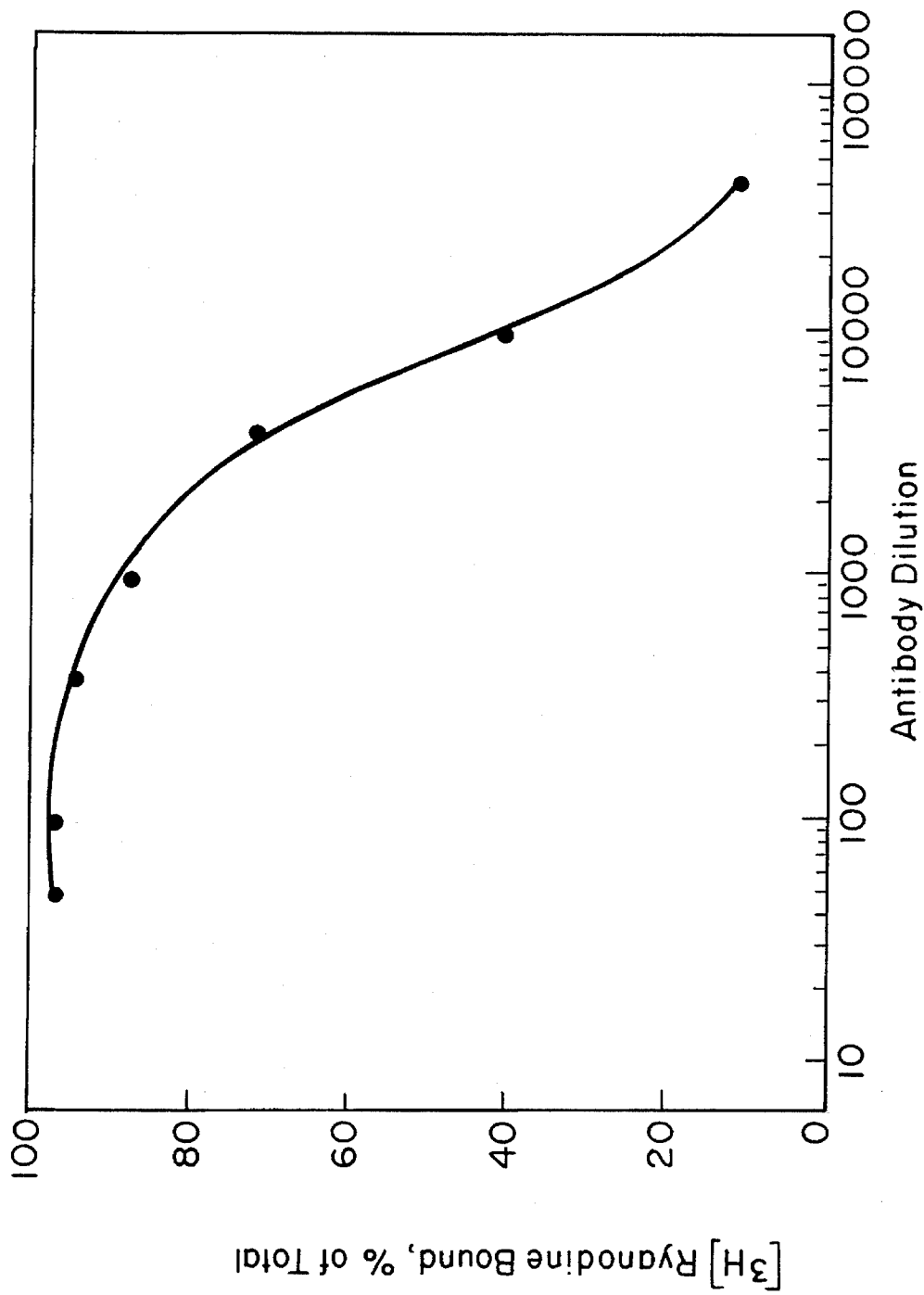
FIG. 3 is a diagram representing a titer test for anti-ryanodine antibodies. Post-immune serum was diluted and added in tubes containing 1 ml of 1 nM [$^3$H]ryanodine in tris-saline gelatin buffer. Dextran-coated charcoal was used for separation of free [$^3$H]ryanodine and antibody-bound [$^3$H]ryanodine. Percent of [$^3$H]ryanodine bound was plotted as a function of antibody dilution.

In order to use the anti-ryanodine antibodies to determine inhibition constants for ryanodine and ryanodine derivatives, it was necessary to determine an appropriate dilution of antibody to use for the competitive radioimmunoassay. A titer test, using serial dilutions of the anti-ryanodine antibodies, was performed to calculate the concentration of antibody required for 50% of the added [$^3$H]ryanodine to be bound in the absence of unlabeled ryanodine. The results of this titer test are shown in FIG. 3. This dilution of antibody was chosen since it has been shown to be appropriate for accurate calculation of the average antibody affinity constant (Muller, Meth. Enzymol. 92: 589–601 (1983)). The titer for the specific antibody used for the competitive radioimmunoassays in this study was determined to be 1:8000 or 0.125 µl/ml.

Affinity and Specificity of Anti-Ryanodine Antibodies

Inhibition of [$^3$H]ryanodine binding was performed using the dextran-coated charcoal assay described above in the presence of unlabeled ryanodine or ryanodine derivatives ($10^{-12}$ to $10^{-5}$M). Ryanodine derivatives were prepared by serial dilution in TSG. The percentage of [$^3$H]ryanodine bound was plotted as a function of the concentration of unlabeled ryanodine compound. The inhibition of [$^3$H]ryanodine at 50% of maximal binding ($IC_{50}$) was determined from the plot.

Figure 4:
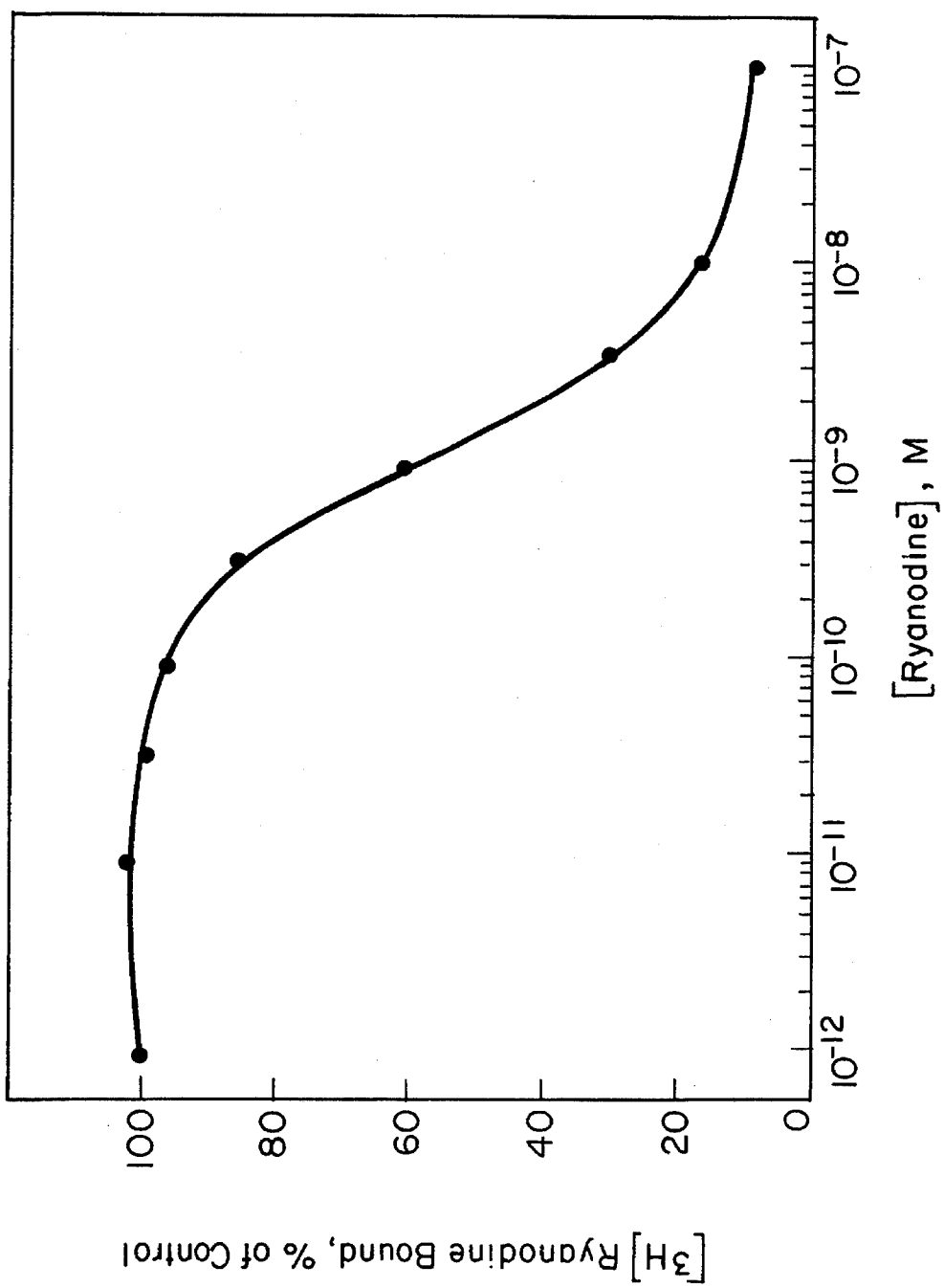
FIG. 4 is a diagram representing the displacement of specifically bound [$^3$H]ryanodine by unlabeled ryanodine. A competitive radioimmunoassay for [$^3$H]ryanodine was performed using the dextran-coated charcoal assay in the presence of 1 nM [$^3$H]ryanodine, a 1:8,000 dilution of anti-ryanodine antibody and various concentrations of unlabeled ryanodine.

FIG. 4 shows the displacement of specifically bound [$^3$H]ryanodine by the addition of increasing concentrations of unlabeled ryanodine. The average antibody apparent dissociation constant ($K_d$) for the [$^3$H]ryanodine-antibody complex, determined according to the method of Müller (in Methods in Enzymology, (Langone and Van Vunakis, Eds.), Vol. 92, pp. 589–601, Academic Press, New York (1983)) was calculated to be 1 nM. This value is similar to the values reported for the ryanodine receptor in skeletal, cardiac and brain membranes.

The specificity of the anti-ryanodine antibodies was tested using various ryanodine derivatives from $10^{-12}$ to $10^{-5}$M as competitors. All ryanodine derivatives were able to compete with the [$^3$H]ryanodine for the antibody binding sites with differences occurring from the substitutions to the basic ryanodine structure as shown in Table 1. Derivatization of the $C_{10}$ hydroxyl of ryanodine gave compounds with $IC_{50}$ values similar to ryanodine, even when the substituents are large (compounds 10, 11 and 12). Comparitively, small S-linked substituents at $C_{21}$ can be tolerated with little effect on the $IC_{50}$ (compound 7). However, more sterically demanding groups reduce binding substantially, notably the mercaptobutyl-linked compounds 4 and 6, which bind about 10 and 100 times less tightly than ryanodine.

[³H]Ryanodine Binding to Rabbit Skeletal Membranes

Rabbit skeletal muscle triads were prepared as previously described (Sharp et al., *J. Biol. Chem.* 262: 12309–12315 (1987)). [³H]Ryanodine binding to triad membranes was performed as described (Imagawa et al., *J. Biol. Chem* 262: 16636–16643 (1987)) using a glass fiber filter assay. Ryanodine and ryanodine derivatives were used at concentrations varying from $10^{-12}$M to $10^{-7}$M in competition assays. The inhibition of [³H]ryanodine at 50% of maximal binding ($IC_{50}$) was determined from a plot of bound [³H]ryanodine versus concentration of competitor.

FIG. 5 shows a comparison of $IC_{50}$ values plotted for [³H]ryanodine competition binding to skeletal membranes and anti-ryanodine antibodies. This figure indicates the similarity in the trend of [³H]ryanodine binding for skeletal membranes and anti-ryanodine antibodies. For example, ryanodine has the highest affinity for membranes and antibodies but Compound 6 has the lowest affinity for both.

EXAMPLE 2

Figure 6B:
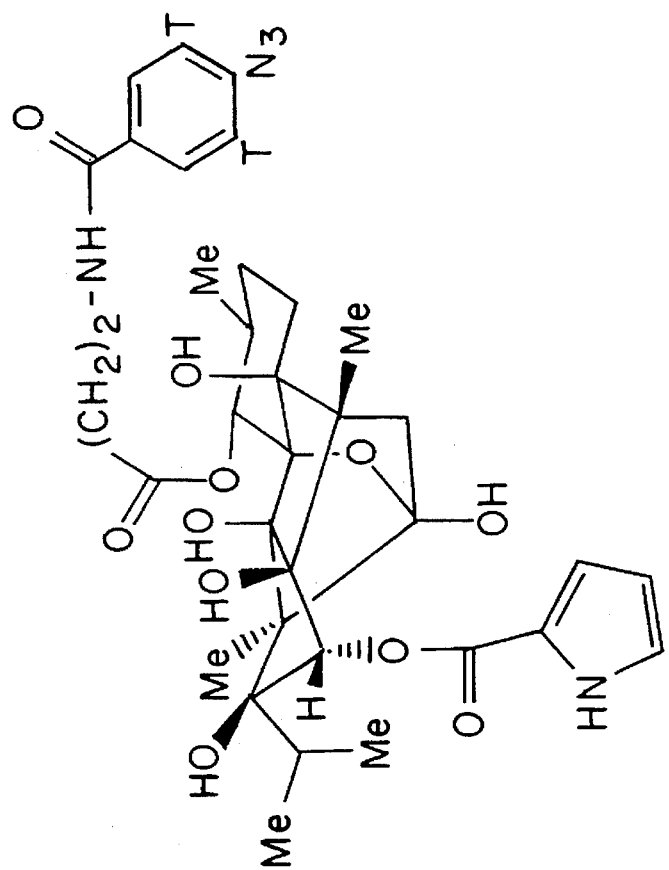
FIG. 6 is a diagram representing a structural comparison between ryanodine and the azido derivative of ryanodine, ABRy. The structure of ryanodine (left) is compared to that of ABRy (right). The location of the tritium atoms on ABRy is designated as "T" in the structure of ABRy.
Figure 6A:
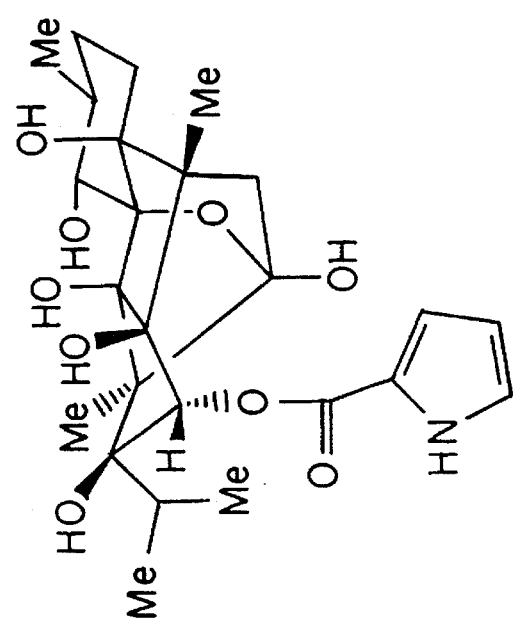

The tritium-labeled photoactivatable ryanodine analog, ABRy, is shown in FIG. 6. The azido derivative of ryanodine, 10-O-(3-[4-Azidobenzamido]-propionyl)-ryanodine (ABRy) was prepared as previously described in Example 1. The azido group, $N_3$, provides this compound with the ability to be covalently crosslinked to proteins. The tritium radiolabeled ABRy compound also contains two tritium atoms (T) on the azidobenzene ring at positions 3 and 5 which makes it possible to detect the specific binding of this compound to various membranes.

This unlabeled compound was provided to Amersham International (England) for production of the radiolabeled compound, [³H]ABRy. The specific activity of [³H]ABRy was 45 Ci/mmol and the radiochemical purity was greater than 93% as determined by thin-layer chromatography on silica gel and reverse phase thin-layer chromatography. [³H]Ryanodine was from Du Pont-New England Nuclear. Horseradish peroxidase-conjugated secondary antibodies were from Boehringer Mannheim. All other chemicals were of reagent grade. This compound contains the same structure as ryanodine except for the addition of an azidobenzamido-propionyl group.

Three different ryanodine receptors genes are expressed in skeletal, cardiac, and brain tissues (for review see McPherson et al., *J. Biol. Chem.* 268, 13765–13768 (1993)). Ryanodine is known to specially bind with high affinity to the skeletal and cardiac $Ca^{2+}$ release channels. This compound also binds with high affinity to the major brain form of the ryanodine receptor which is the cardiac isoform (McPherson and Campbell, *J. Biol. Chem.* 268, 19785–19790 (1993); and Witcher et al., *J. Biol. Chem.* 267, 4963–4967 (1992)).

In order to characterize the binding of [³H]ABRy to the different ryanodine receptors, Scatchard analysis was performed on skeletal muscle triads. Triads were purified from rabbit skeletal muscle as previously described (Sharp et al., *J. Biol. Chem.* 262, 12309–12315 (1987)). Isolated triad membranes (50 µg) were incubated with 0.5 to 50 nM [³H]ABRy for 1 hr at 37° C. in the presence or absence of 10 µM ABRy in 250 µl of 10 mM sodium HEPES, pH 7.4 containing 0.5M KCl, 10 mM ATP, and 0.8 µM $CaCl_2$ (50 µM free $Ca^{2+}$). The proteins were collected on Whatman GF-B filters using a Brandel Cell Harvester. For specific experiments, the concentrations of ATP, $Ca^{2+}$, and KCl were varied individually while keeping all other variables constant. The concentration of free divalent cations was determined using the computer program of Fabiato (*Methods Enzymol.* 157, 378–420 (1988)).

Figure 7:
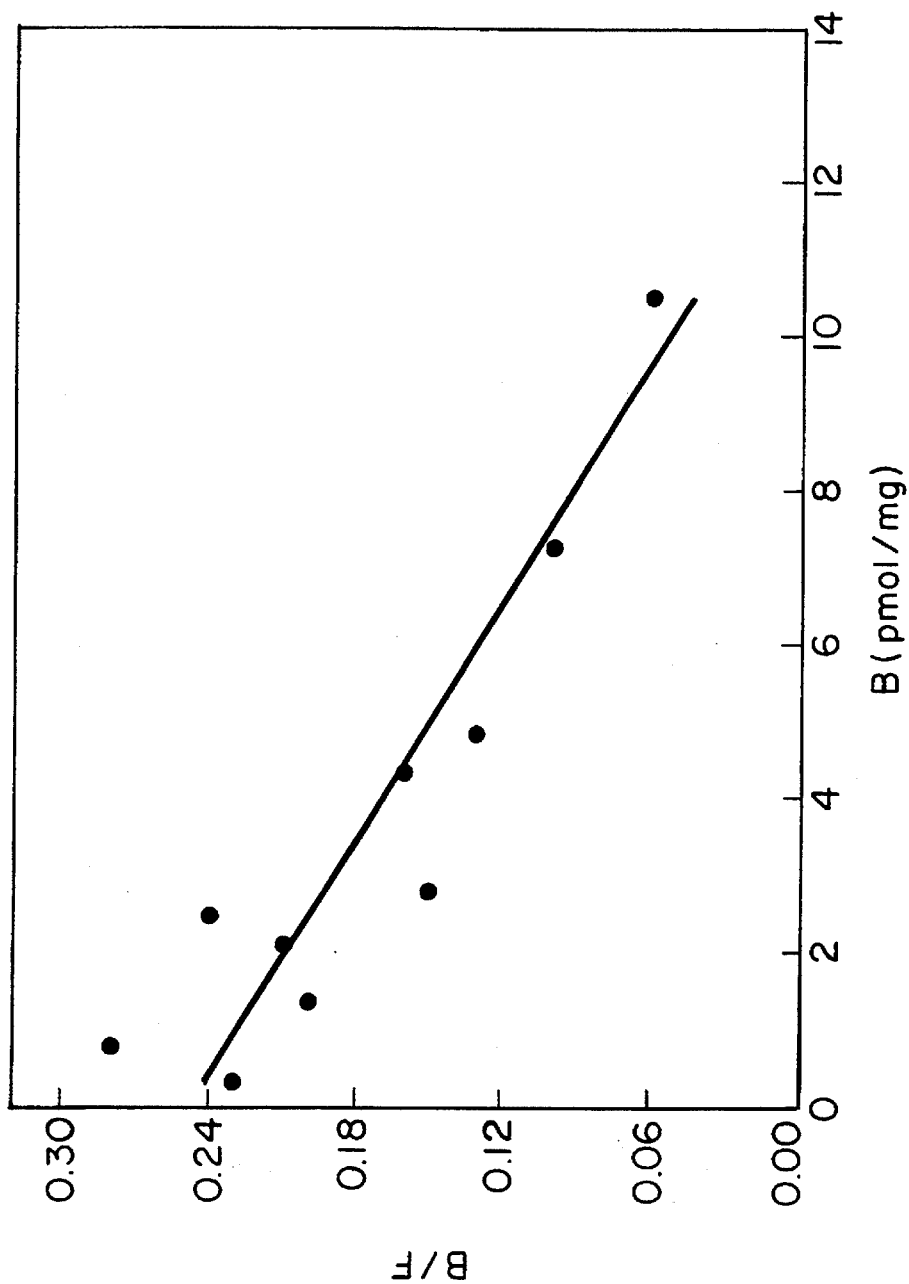
FIG. 7 is a diagram representing results of Scatchard analysis of [$^3$H]ABRy binding to skeletal muscle triads. Triad membranes (50 μg) were incubated with various concentrations of [$^3$H]ABRy (0.5 to 50 nM) for 1 hr at 37° C. as described below. Specific binding was determined in the presence of 10 μm unlabeled ryanodine.

[³H]ABRy (0.5–50 nM) bound to skeletal muscle triads in a saturable manner. Scatchard plots of typical experiments for [³H]ABRy binding used 50 µg of triads (FIG. 7). Nonspecific binding was determined in the presence of 10 µM ryanodine. The values for $K_d$ and $B_{max}$ for triads (determined from three separate experiments), were 5.5 nM and 12.7 pmol/mg, respectively. These data demonstrate that [³H]ABRY binds with high affinity to a single class of receptors in triad membranes. These $K_d$ and $B_{max}$ values for [³H]ABRy are very similar to the values obtained for [³H]ryanodine binding in skeletal muscle triads (Imagawa et al., *J. Biol. Chem.* 262, 1740–1747 (1987)).

Figure 8A:
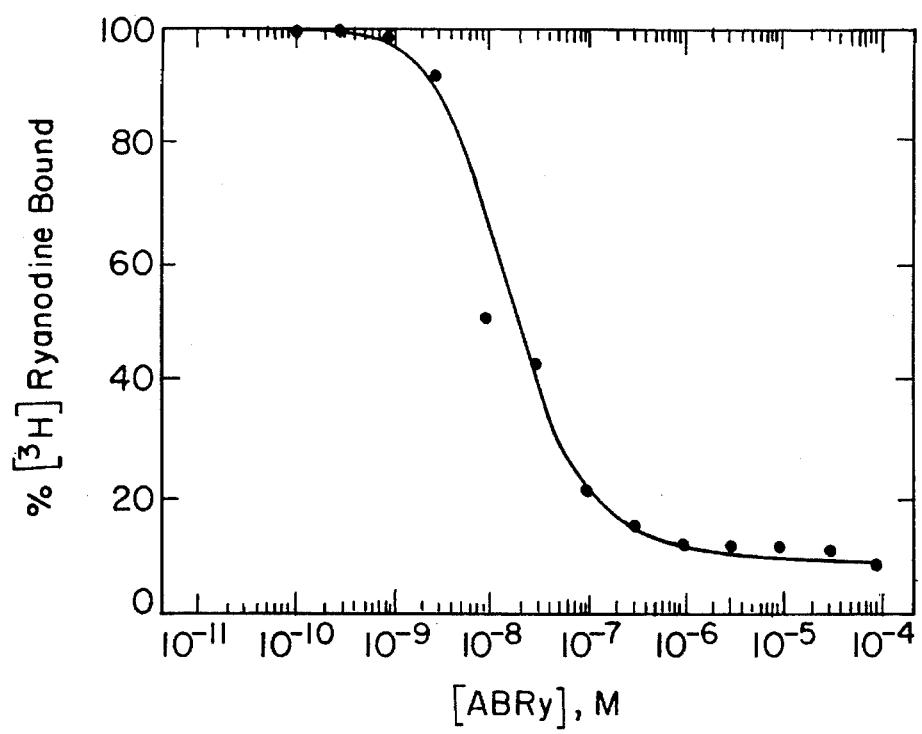
FIGS. 8 is a diagram representing competition of [$^3$H] ryanodine binding to skeletal, cardiac, and brain membranes with unlabeled ABRy. (A) Skeletal muscle triads (10 μg), (B) total cardiac microsomes (200 μg), or (C) crude brain microsomes (500 μg) were incubated with increasing concentrations of unlabeled ABRy in the presence of 1 nM [$^3$H]ryanodine for 1 hr at 37° C. as described below. Binding of 100% was defined by the amount of [$^3$H]ryanodine specifically bound in the presence of the lowest concentration of ABRy.
Figure 8B:
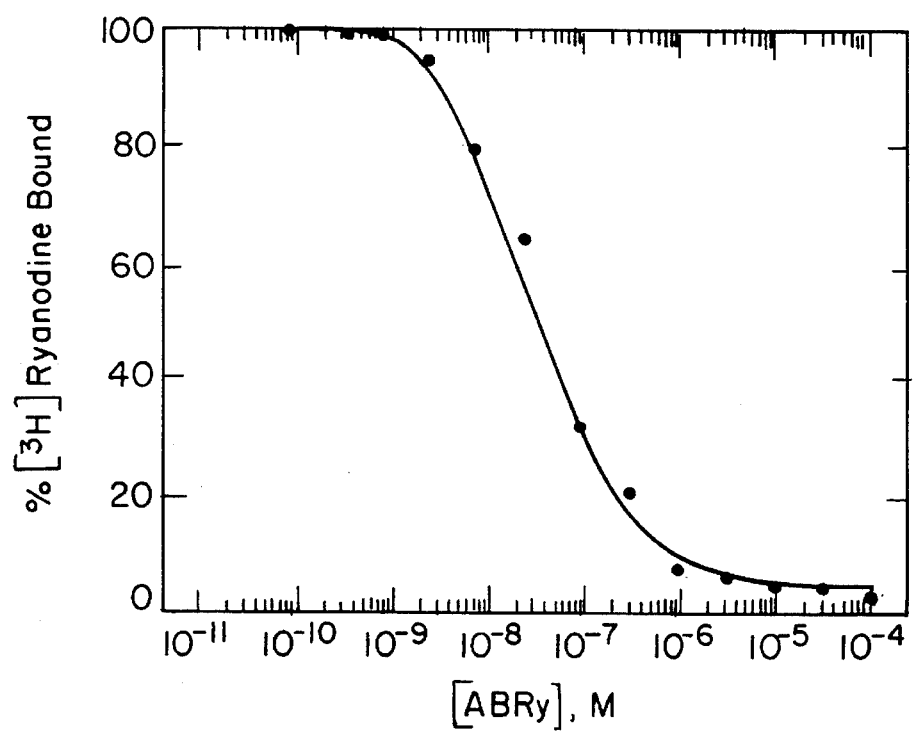
Figure 8C:
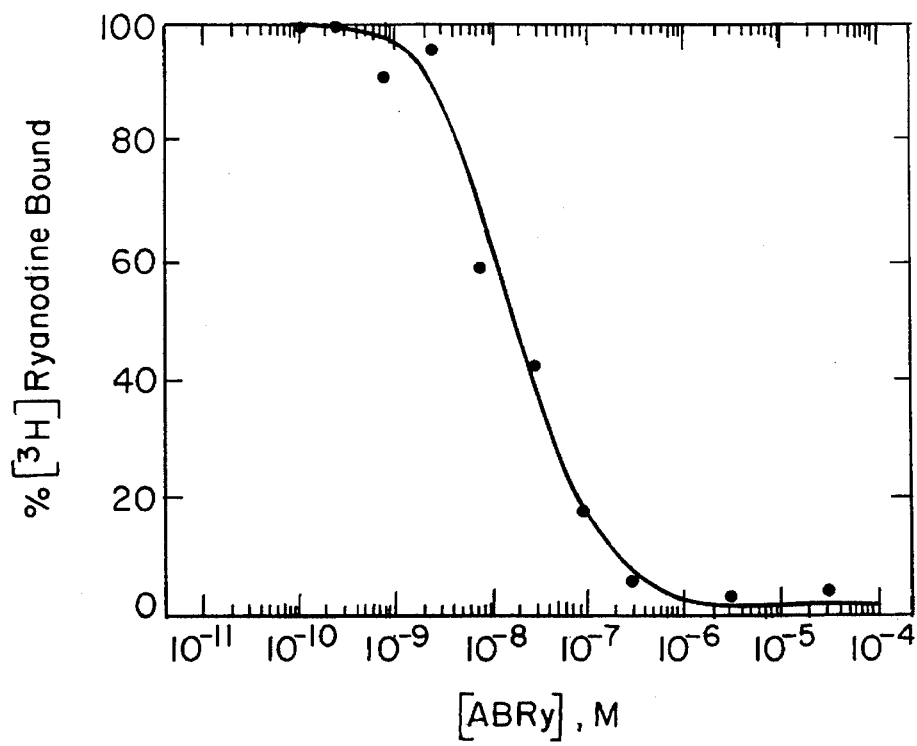

To determine if [³H]ABRy bound to the same site on the $Ca^{2+}$ release channel in skeletal, cardiac, and brain membranes as did [³H]ryanodine, competition binding experiments were performed with [³H]ryanodine in the presence of increasing concentrations of ABRy. Canine cardiac junctional SR vesicles were isolated as described previously (Witcher et al., *J. Biol. Chem.* 266, 1114–11152 (1991)). Crude rabbit brain membranes were purified as previously described (Witcher et al., *J. Biol. Chem.* 267, 4963–4967 (1992)). FIG. 8A shows that unlabeled ABRy specifically inhibited [³H]ryanodine binding to triads with a half-maximal inhibition at approximately 37 nM. The half-maximal inhibition of [³H]ryanodine binding to cardiac and brain membranes were 89 nM and 25 nM, respectively (FIGS. 8B– C). These values are in the same range as the half-maximal inhibition of [³H]ryanodine binding to triads by ryanodine which is approximately 20.0 nM and demonstrate that ABRy binds to the ryanodine receptor at the same site as [³H]ryanodine.

Figure 9A:
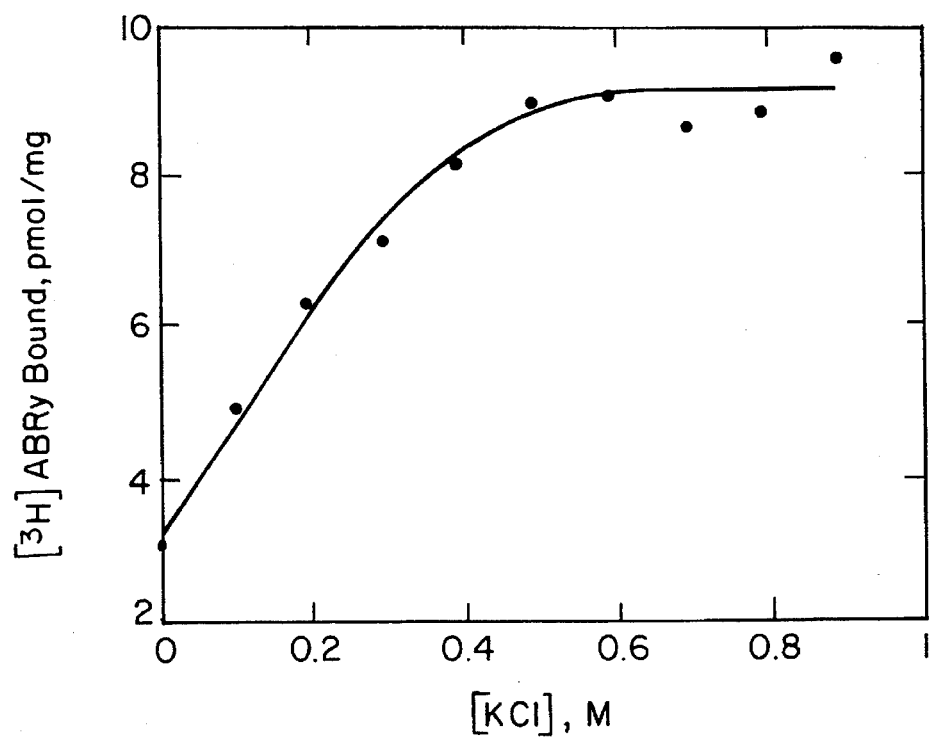
FIG. 9 is a diagram representing analysis of $Ca^{2+}$, ATP, and KCl effects on [$^3$H]ABRy binding to skeletal muscle membranes. [$^3$H]ABRy binding was performed on skeletal muscle triads in the presence of increasing concentrations of (A) KCl, (B) ATP, and (C) $Ca^{2+}$ as described below.
Figure 9B:
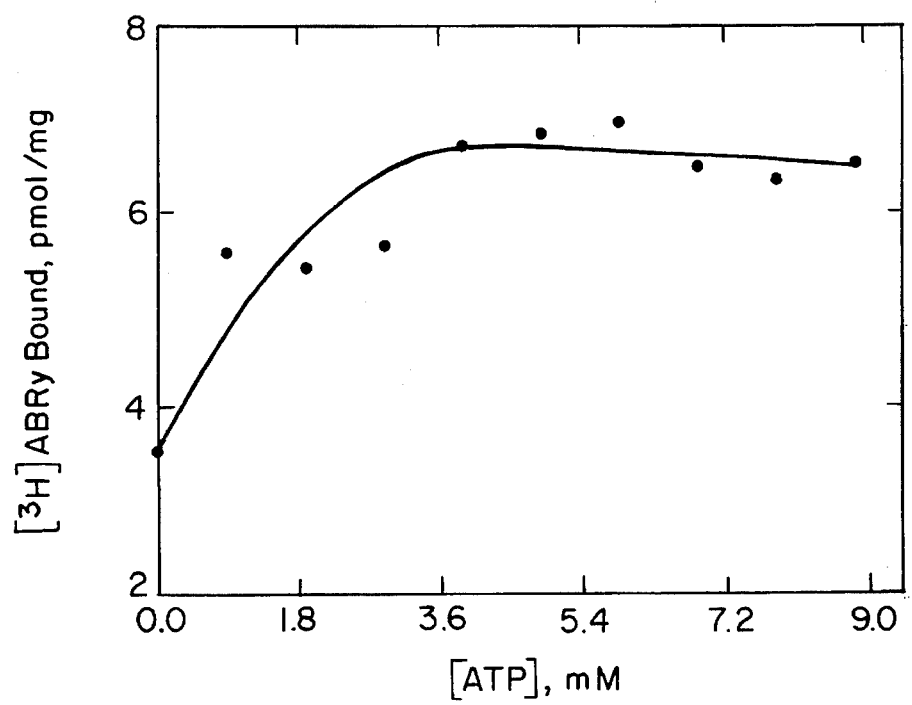

A number of compounds have been shown to modulate [³H]ryanodine binding to the $Ca^{2+}$ release channel. Increasing concentrations of both KCl and ATP dramatically stimulate [³H]ryanodine binding to all forms of the ryanodine receptor. To further characterize the interaction between ABRy and the skeletal ryanodine receptor, [³H]ABRy binding analysis to triads in the presence of KCl and ATP was performed. [³H]ABRy binding to the skeletal ryanodine receptor is sensitive to changes in ionic strength as demonstrated by the increased binding in the presence of increasing KCl concentrations (FIG. 9A). Binding was maximally stimulated 3-fold at a concentration of 0.9M KCl. This effect is similar to that observed for [³H]ryanodine binding to both triads and the purified skeletal ryanodine receptor (Inui et al., *J. Biol. Chem.* 262, 1740–1747 (1987)). [³H]ABRy binding to skeletal muscle triads is also sensitive to ATP, which can maximally increase ABRy binding at 4.5 mM (FIG. 9B). [³H]Ryanodine binding to the skeletal ryanodine receptor is also stimulated by millimolar concentrations of adenine nucleotides (Michalak et al., *Biochim. Biophys. Act.* 939, 587–594 (1988)). It has also been shown that millimolar concentrations of ATP stimulate the rate of $Ca^{2+}$ release from both skeletal and cardiac muscle SR vesicles (Meissner et al., *Biochemistry* 25, 236– 244 (1986); and Rousseau and Smith, *Biophys. J.* 50, 1009– 1014 (1986)) and increase the channel activity of both receptors in planar lipid bilayers (Lai et al., *Nature* 331, 315–3193 (1988) and Rousseau and Smith, *Biophys. J.* 50, 1009–1014 (1986)).

Figure 9C:
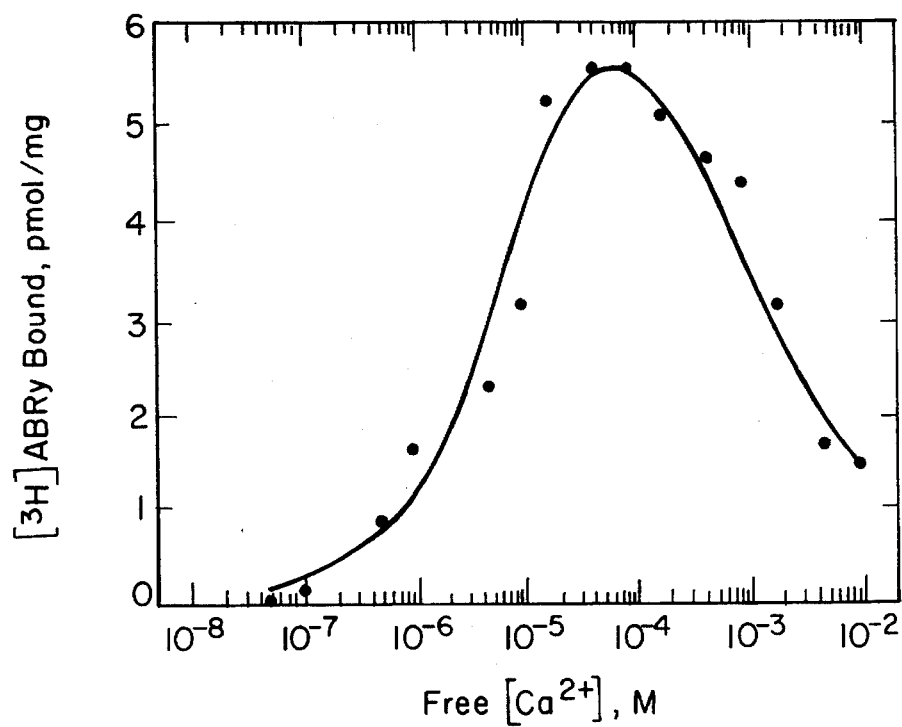

Because $Ca^{2+}$ is an important regulator of $Ca^{2+}$ release from the ryanodine receptor, the effect of $Ca^{2+}$ concentrations on the binding of [³H]ABRy to skeletal muscle triads was examined. $Ca^{2+}$ increases [³H]ABRy binding to the skeletal muscle ryanodine receptor at concentrations between 100 nM and 100 µM (FIG. 9C). The half maximal stimulation of [³H]ABRy binding occurs at approximately 5 µM. This bell shaped $Ca^{2+}$ response curve (FIG. 9C) is very similar to the effect of $Ca^{2+}$ on [³H]ryanodine binding to skeletal, cardiac, and brain ryanodine receptors.

Since [³H]ABRy contains a photoactivatable azido group, this compound was used to covalently label skeletal muscle triads following equilibrium binding. Skeletal muscle triads (250 µg) were incubated in the dark with 15 nM [³H]ABRy for 1 hour at 37° C. in the presence or absence of 10 µM ryanodine in 1 ml of 10 mM sodium HEPES, pH 7.4 containing 0.5M KCl, 10 mM ATP, and 0.8 mM $CaCl_2$ (50 µM free $Ca^{2+}$). The membranes were then pelleted at 400,000×g for 15 min and resuspended in 1 ml of the binding buffer with 5 mM glutathione. The samples were placed in a plastic petri dish at 4° C. and were exposed to UV light (365 nm) at a distance of 1 cm for 45 min. The membranes were then centrifuged in a microfuge at maximum speed for 15 min. at 4° C. The pellets were resuspended in Laemmli sample buffer.

The proteins were then analyzed by SDS-PAGE (3–12% gradient gels) using the buffer system of Laemmli (*Nature* 227, 680–685 (1970)). Gels were stained with Coomassie blue or transferred to nitrocellulose for immunoblot analysis as previously described (Witcher et al., *Science* 261, 486–489 (1993)). Specific polyclonal antibodies against the C-terminal 15 amino acid peptide of the skeletal ryanodine receptor (Rabbit 46) (McPherson et al., *Neuron* 7, 17–25 (1991)) were affinity purified from Immobilon-P transfer strips of the cardiac ryanodine receptor. Gels used for fluorography were first stained with Coomassie blue, destained, soaked in Enlightning (DuPont), and dried under vacuum. The dried gels were then exposed to Kodak XAR-5 film at −80° C. The fluorograms were also analyzed densitometrically using a Molecular Dynamics Model 300A scanning densitometer.

In the presence of UV light, [³H]ABRy covalently binds to the skeletal muscle ryanodine receptor. Covalent incorporation of [³H]ABRy into the skeletal muscle ryanodine receptor was abolished with excess unlabeled ryanodine (10 µM). The identity of a protein band as the skeletal muscle ryanodine receptor was confirmed by immunoblot analysis and by immunoprecipitation with affinity-purified polyclonal antibodies to the ryanodine receptor.

A smaller band just below the 560 kDa protein (approximately 500 kDa) which was identified by photocoupled [³H]ABRy and affinity-purified antibodies against the ryanodine receptor is a known proteolytic fragment of the receptor. Photolabeling experiments performed in the presence of magnesium and ruthenium red, at concentrations known to inhibit ryanodine binding, abolished the [³H]ABRy labeling of the skeletal muscle ryanodine receptor.

In order to further define the ryanodine binding site, tryptic digestion of the [³H]ABRy-photolabeled skeletal muscle ryanodine receptor was performed to identify proteolytic fragments containing the ABRy binding site. Skeletal muscle triads (250 µg) were prelabled with [³H]ABRy as described above. Membranes were then resuspended (2 mg/ml) in 50 mM ammonium bicarbonate and incubated with trypsin (1:1000, enzyme:membranes, w/w) for 1, 10 and 15 min. at RT. In control experiments, trypsin was omitted. Reactions were terminated by the addition of Laemmli sample buffer, followed by boiling for 2 min.

The appearance of a 76 kDa fragment was observed after trypsin digestion which bound the [³H]ABRy and was also identified with affinity-purified C-terminal polyclonal antibodies against the ryanodine receptor. Recently, it has been demonstrated that one of the major tryptic fragments resulting from a partial digestion of the ryanodine receptor was a 76 kDa fragment which contained the carboxyl portion of the receptor. The results disclosed herein are consistent with this observation and also demonstrates that the 76 kDa C-terminal fragment, which is likely to contain transmembrane domains, is critical for the formation of the high affinity ryanodine binding site. Also a known modulator of ryanodine binding, ATP, has also been demonstrated to bind to similar 76 kDa fragment of the ryanodine receptor after partial tryptic digestion. It is possible that the 76 kDa tryptic fragment which is critical in forming the high affinity ryanodine binding site also is involved in the binding of ATP.

Salama et al. has suggested that ryanodine also interacts with a 106 kDa protein present in the sarcoplasmic reticulum of skeletal muscle (Salama et al., *Cell Calcium* 13, 635–647 (1992)). In planner lipid bilayers, ryanodine was thought to affect this sulfydryl-gated protein at concentrations (nanomolar) which would suggest a high affinity interaction between ryanodine and the 106 kDa protein (Hilkert et al., *Arch. Biochem. Biophys.* 292, 1–15 (1992)). While this protein may be involved in the function of the sarcoplasmic reticulum, the results disclosed herein demonstrates that ABRy, which shares high structural homology with ryanodine, only is capable of binding to the 565 kDa ryanodine receptor/$Ca^{2+}$ release channel.

The data presented here indicates that the tritiated, photoactivable derivative of ryanodine, ABRy, interacts directly and specifically to the active ryanodine binding site on the $Ca^{2+}$ release channel. The results also demonstrate that the binding of [³H]ABRy to the skeletal muscle ryanodine receptor is allosterically regulated by KCl, ATP, and $Ca^{2+}$, compounds known to directly affect $Ca^{2+}$ release from the ryanodine receptor. The identification of the 76 kDa C-terminal tryptic fragment of the skeletal muscle ryanodine receptor covalently binding [³H]ABRy illustrates that this region of the $Ca^{2+}$ release channel is critical in the formation of the high affinity ryanodine binding site. Localization of the ryanodine binding site will provide new information on the structure and functional relationship between ryanodine and the $Ca^{2+}$ release channel. This information will be useful in determining if this binding site is conserved among the different ryanodine receptor gene products. The identification of the ryanodine binding site could also provide information on how ryanodine and other modulators of the $Ca^{2+}$ release channel affect channel function, and could possibly help determine the structure of the $Ca^{2+}$ channel pore.

We claim:

1. An immunogenic derivative of ryanodine which, following immunization of a mammal, stimulates the production of antibodies which bind specifically to ryanodine with an $IC_{50}$ of less than $10^{-8}$, the immunogenic derivative of ryanodine being characterized by the following structure:

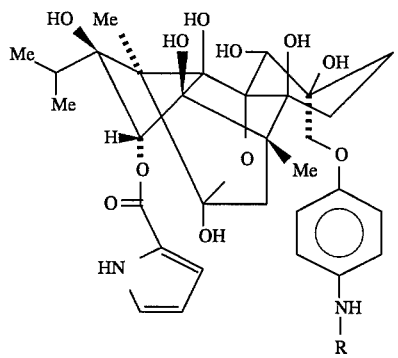

wherein R is an immunogenic protein carrier.

2. The immunogenic derivative of claim 1 wherein the immunogenic protein carrier has a molecular weight of at least 4,000.

3. The immunogenic derivative of claim 2 wherein the immunogenic protein carrier is selected from the group consisting of bovine serum albumin, casein, ovalbumin or keyhole limpet hemocyanin.

4. A labeled affinity reagent which binds to the ryanodine receptor with an $IC_{50}$ of less than about $10^{-6}$, the labeled affinity reagent being selected from the group consisting of labeled forms of 21-(2-[3,3,3-Trifluoro-2-diazopropionyloxy]-ethylmercapto)-ryanodine and 21-(4-Hydroxybutylmercapto)-ryanodine.

5. A labeled affinity reagent which binds to the ryanodine receptor with an $IC_{50}$ of less than about $10^{-7}$, the labeled affinity reagent being selected from the group consisting of labeled forms of 10-O-(3-[4-Azidobenzamido]-propionyl)-ryanodine; 10-O-(3-[2-Nitro-5-azidobenzamido]-propionyl)-ryanodine; and 10-O-(3-[4-benzoylbenzamido]-propionyl)-ryanodine.

6. A method for identifying the ryanodine binding site on the ryanodine receptor, comprising:

a) providing a labeled affinity reagent which binds to the ryanodine receptor with an $IC_{50}$ of less than about $10^{-7}$;

b) incubating the labeled affinity reagent with the ryanodine receptor under conditions appropriate for specific binding of the affinity labeling reagent to the ryanodine receptor, thereby forming an affinity binding complex;

c) chemically linking the components of the affinity binding complex by exposing the complex to ultraviolet light of a wavelength appropriate to activate the affinity labeling reagent;

d) digesting the affinity binding complex to generate peptide fragments; and e) identifying the peptide binding fragment to which the labeled affinity reagent is linked.

7. The method of claim 6 wherein the labeled affinity reagent is 10-O-(3-[4-Azidobenzamido]-propionyl)-ryanodine which is radiolabeled.

8. The labeled affinity reagent of claim 4 wherein the labeled affinity reagent is labeled with a radiolabel.

9. The labeled affinity reagent of claim 5 wherein the labeled affinity reagent is labeled with a radiolabel.

* * * * *